United States Patent [19]

Bezwada

[11] Patent Number: 5,442,033
[45] Date of Patent: Aug. 15, 1995

[54] LIQUID COPOLYMERS OF EPSILON-CAPROLACTONE AND LACTIDE

[75] Inventor: Rao S. Bezwada, Whitehouse Station, N.J.

[73] Assignee: Ethicon, Inc., Somerville, N.J.

[21] Appl. No.: 339,045

[22] Filed: Nov. 14, 1994

Related U.S. Application Data

[63] Continuation-in-part of Ser. No. 317,684, Oct. 5, 1994, abandoned, which is a continuation of Ser. No. 95,128, Jul. 20, 1993, abandoned.

[51] Int. Cl.$^6$ ............................................. C08G 63/08
[52] U.S. Cl. .................................. 528/354; 525/408; 525/411; 525/415
[58] Field of Search ............... 528/354, 357, 361; 525/408, 411, 415

[56] References Cited

U.S. PATENT DOCUMENTS

| | | | |
|---|---|---|---|
| 4,030,499 | 6/1977 | Bacato | 424/19 |
| 4,304,767 | 12/1981 | Heller et al. | 424/78 |
| 4,655,777 | 4/1987 | Dunn et al. | 623/16 |
| 4,719,246 | 1/1988 | Murdoch et al. | 521/134 |
| 4,766,182 | 8/1988 | Murdoch et al. | 525/413 |
| 4,791,929 | 12/1988 | Jarrett et al. | 528/361 |
| 4,800,219 | 1/1989 | Murdoch et al. | 525/413 |
| 4,902,515 | 2/1990 | Loomis et al. | 424/486 |
| 4,981,696 | 1/1991 | Loomis et al. | 424/486 |
| 5,030,457 | 7/1991 | Ng et al. | 424/486 |
| 5,047,048 | 9/1991 | Bezwada et al. | 606/231 |
| 5,053,485 | 10/1991 | Wieuwenhuis et al. | 528/354 |
| 5,250,584 | 10/1993 | Ikada et al. | 523/354 |

FOREIGN PATENT DOCUMENTS

0509203A3 4/1993 European Pat. Off. ...... C08G 63/08
WO92/07555 5/1992 WIPO.

*Primary Examiner*—Melvyn I. Marquis
*Assistant Examiner*—Shelley A. Dodson
*Attorney, Agent, or Firm*—Hal B. Woodrow

[57] ABSTRACT

A copolymer of from in the range of from about 55 to about 70 weight percent lactide and from in the range of from about 45 to about 30 mole percent ε-caprolactone suitable for use in biomedical applications such as drug delivery, coatings for surgical sutures and needles, and lubricants for medical devices.

5 Claims, No Drawings

LIQUID COPOLYMERS OF EPSILON-CAPROLACTONE AND LACTIDE

This is a continuation-in-part of Ser. No. 317,684 filed Oct. 5, 1994, now ABN (that is hereby incorporated by reference herein), which is a continuation of Ser. No. 08/095,128 filed Jul. 20, 1993 abandoned.

FIELD OF THE INVENTION

This invention relates to absorbable liquid or low melting copolymers of ε-caprolactone and lactide. More specifically, it relates to liquid copolymers of caprolactone and lactide suitable for use in biomedical applications such as drug delivery, coatings for surgical sutures and needles and lubricants for medical devices.

BACKGROUND OF THE INVENTION

Pharmaceuticals have been conventionally administered, either in oral or parenteral dosage forms. However, these dosage forms are not always well suited for particular drugs or prolonged drug therapies. Many pharmaceuticals cannot be administered orally and patient noncompliance with dosage instructions is also a significant problem with oral dosage forms. To overcome these and other short comings of these dosage forms several new dosage forms have recently been developed.

The most notable recent development has been the use of bioerodible or bioabsorbable polymer matrices as carriers for implantable or intrauterine devices. Several publications describe these materials such as U.S. Pat. No. 4,304,767 to Heller et al., "Biodegradable block copolymer matrices for long-acting contraceptives with constant release" J. Contr. Rel. 32 (1992) 3–14 by Z. W. Gu et al., and U.S. Pat. No. 5,030,457 to Ng.

Heller describes a family bioabsorbable poly(ortho esters) which may be used as a matrix for controlled drug release. The polymers Heller et al. describes are synthesized by reacting a polyol with a diketene acetal. The polymers produced by this synthesis tend to be rigid because of the pentaerythritol segments in the polymer backbone. Unfortunately, this limits the use of these polymers to solid implants which generally must be surgically implanted.

Similarly, Gu et al. describes hard microspheres triblock copolymer of poly(e-caprolactone-co-DL-lactide-co-glycolide) for the controlled release of contraceptives. The microspheres that Gu et al., describes are designed to be injected thereby avoiding the need to surgically implant a solid dosage. Unfortunately, these copolymers must be formed into microspheres and the kinetics of the pharmaceutical release are complicated by the different release mechanisms of the individual blocks of the triblock copolymer.

Ng describes a bioerodible polymer poly(ortho ester) formed from a one step reaction of a ortho ester and a triol. These polymer are more flexible than the polymers described by Heller and can be employed in ointments, gels and creams. Unfortunately the poly(ortho esters) described by Ng are highly susceptible to acid hydrolysis which limits their utility as a carrier for acidic pharmaceuticals.

Thus it would be a significant contribution to the art to provide a bioabsorbable polymer that is easy to administer and slowly hydrolyses as it releases a drug.

SUMMARY OF THE INVENTION

In one aspect, the invention is a pharmaceutical carrier comprising a random copolymer of from 55 to 70 percent by mole lactide and from 45 to 30 mole percent ε-caprolactone. These low melting or liquid copolymers may be used as carriers for a variety of pharmaceutical compounds.

The copolymers of this invention are also useful for other biomedical applications. For example, the copolymers may be used as coatings for surgical sutures, surgical needles or as lubricants for medical devices such as trocars.

DETAILED DESCRIPTION OF THE INVENTION

The random copolymers of this invention are composed of lactide and ε-caprolactone within a range suitable to provide a liquid or soft solid a room temperature. The amount of lactide contained in the copolymer carriers of this invention will be in the range of from about 55 to about 70 mole percent and the amount of ε-caprolactone will be in the range of from about 45 to 30 mole percent of the copolymer (where the total of the mole percents is 100). Preferably, the amount of lactide in the copolymer will be in the range of from 55 to 65 mole percent and the amount of ε-caprolactone will be in the range of from 45 to 35 mole percent (where the total of the mole percents is 100).

The copolymer carriers of this invention are typically characterized by being liquids at room temperature (25° C.) or low melting points solids (being liquids between 35° C. and 25° C.). The copolymers of the present invention have an intrinsic viscosity as determined in a 0.1 g/dl solution of hexafluoroisopropanol (HFIP) at 25° C. ranging from about 0.05 to less than 0.8, preferably from about 0.05 to about 0.3 and most preferably from 0.05 to 0.2 A copolymer with an intrinsic viscosity below 0.05 may fail to significantly impart a controlled release profile to a pharmaceutical, and a carrier copolymer with an intrinsic viscosity above 0.8 may be too viscous to be easily administered.

The copolymers of this invention may be mixed with one or more therapeutic agents. The preferred dosage forms for the copolymer of the invention are sustained release parenterals, bioerodible ointments, gels, creams, and similar soft dosage forms adapted for the parenteral or topical administration of therapeutic agents, other modes of administration (e.g., transdermal) and compositional forms (e.g., more rigid transdermal forms) are within the scope of the invention as well.

Parenteral administration of a bioerodible composition of the invention can be effected by either subcutaneous, or intramuscular injection. Parenteral formulations of the copolymer may be formulated by mixing one or more pharmaceuticals with a liquid copolymer. Other suitable parenteral additives may be formulated with the copolymer and pharmaceutical active, however, if water is to be used it should be added immediately before administration. The bioerodible ointment, gel or cream may also be injected as is or in combination with one or more suitable auxiliary components as described below. Parenteral delivery is preferred for administration of proteinaceous drugs such as growth factors, growth hormone, or the like.

The bioerodible ointments, gels and creams of the invention will include: an ointment, gel or cream base comprising one or more of the copolymers described herein and a selected therapeutic agent. The therapeutic agent, whether present as a liquid, a finely divided solid, or any other physical form, is dispersed in the ointment, gel or cream base. Typically, but optionally, the compositions include one or more other components, e.g., nontoxic auxiliary substances such as colorants, diluents, odorants, carriers, excipients, stabilizers or the like.

The amount of active agent will be dependent upon the particular drug employed and condition being treated. Typically the amount of drug represents about 0,001% to about 70%, more typically about 0.001% to about 50%, most typically about 0.001% to about 20% by weight of the total composition being common.

The quantity and type of copolymers incorporated into the parenteral, ointment, gel, cream, etc., is variable. For a more viscous composition, a higher molecular weight polymer is used. If a less viscous composition is desired, a lower molecular weight polymer can be employed. The product may contain blends of the liquid or low melting point copolymers to provide the desired release profile or consistency to a given formulation.

While not essential for topical or transdermal administration of many drugs, it may in some cases, with some drugs, be preferred that a skin permeation enhancer be coadministered therewith. Any number of the many skin permeation enhancers known in the art may be used. Examples of suitable enhancers include dimethylsulfoxide (DMSO), dimethylformamide (DMF), N,N-dimethylacetamide (DMA), deslymethylsulfoxide ($C^{10}MS$)), ethanol, eucalyptol, lecithin, and the 1-N-dodecylcyclazacycloheptan-2-ones (available under the trademark Azone ®from the Nelson Research and Development Company, Irvine, Calif.).

The variety of different therapeutic agents which can be used in conjunction with the copolymers of the invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and betablockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers. Suitable pharmaceuticals for parenteral administration are well known as is exemplified by the *Handbook on Injectable Drugs*, 6th edition, by Lawrence A. Trissel, American Society of Hospital Pharmacists, Bethesda, Md., 1990 (hereby incorporated by reference).

In two particularly preferred embodiments the therapeutic agents for administration in conjunction with the bioerodible polymers of the invention are antibacterial agents for the treatment of deep wounds, and antibiotics for periodontal treatment (e.g., tetracycline or the like). Other preferred drugs for use with the presently disclosed polymers include proteinaceous drugs such as epidermal growth factors or growth hormones.

Depending on dosage form, the pharmaceutical compositions of the preceding section may be administered in different ways, i.e., parenterally, topically, or the like. Preferred dosage forms are liquid dosage forms which can be administered parenterally.

The copolymers, upon contact with body fluids including perspiration, saliva, or the like (depending upon the mode of administration), undergoes gradual bioerosion with concomitant gradual exposure of the dispersed drug to the afflicted tissue. This can result in prolonged delivery (over, say 1 to 10,000 hours, preferably 2 to 1000 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Topical application can be enhanced by occlusion, i.e., placing a barrier over the area treated so as to enhance absorption into the skin. Topical administration is preferred for wound healing and in the treatment of periodontal disease.

The following examples illustrate but are not intended to limit the scope of the claimed invention.

EXAMPLE 1

LIQUID COPOLYMERS OF ε-CAPROLACTONE/L(−) LACTIDE @ 45/55 BY MOLE PERCENT INITIAL COMPOSITION

A flame dried, 250 ml, round bottom single neck flask was charged with 51.36 gm (0.45 mole) of ε-caprolactone, 79.27 gm. (0.55 mole) of L(−)lactide, 3.67 milliliters of propylene glycol (USP grade), and 0.101 milliliters of stannous octaote (0.33 molar in toluene). The flask was fitted with a flame dried mechanical stirrer. The reactor flask was purged with nitrogen three times before venting with nitrogen. The reaction mixture was heated to 160° C. and maintained at this temperature for about 20 hours. The copolymer was dried under vacuum (0.1 mm Hg) at 110° C. for about 7 hours to remove any unreacted monomer. The copolymer had an inherent viscosity of 0.22 dl/g in hexafluoroisopropanol (HFIP) at 25° C. The copolymer was a liquid at room temperature. The mole ratio of poly[ε-caprolactone]/poly[lactide]/caprolactone/propylene glycol ester was found to be 44.8/50.8/1.2/3.2 by NMR.

EXAMPLE 2

LIQUID COPOLYMERS OF ε-CAPROLACTONE/L(−)LACTIDE @ 40/60 BY MOLE PERCENT INITIAL COMPOSITION

The procedure in Example 1 was substantially repeated, except that 45.66 gm (0.40 mole) of ε-caprolactone, 86.48 g (0.60 mole) of L(−) lactide were used. The copolymer was dried under vacuum (0.1 mm Hg) at 110° C. for about 7 hours to remove any unreacted monomer, The copolymer had an inherent viscosity of 0.38 dl/g in hexafluoroisopropanol (HFIP) at 25° C., The copolymer was a liquid at room temperature, The mole ratio of poly[ε-caprolactone]/poly[lactide]/caprolactone/propyleneglycol ester was found to be 40.0/54.2/1.9/3.9 by NMR.

EXAMPLE 3

LIQUID COPOLYMERS OF ε-CAPROLACTONE/L(−)LACTIDE @ 35/65 BY MOLE PERCENT INITIAL COMPOSITION

The procedure in Example 1 was substantially repeated, except that 39.95 gm (0.35 mole) of ε-caprolactone, 93.68 g (0.65 mole) of L(−) lactide are used. The copolymer was dried under vacuum (0.1 mm Hg) at 110° C. for about 7 hours to remove any unreacted monomer. The copolymer had an inherent viscosity of 0.19 dl/g in hexafluoroisopropanol (HFIP) at 25° C. The copolymer was a liquid at room temperature. The mole ratio of poly [ε-caprolactone]/poly [lactide ]/caprolactone/propyleneglycol ester was found to be 35.6/59.5/1.2/3.7 by NMR.

EXAMPLE 4

LIQUID COPOLYMERS OF ε-CAPROLACTONE/L(−)LACTIDE @ 45/55 BY MOLE PERCENT INITIAL COMPOSITION

The procedure in Example 1 was substantially repeated, except that 6.0 milliliters of glycerol (USP grade) was used instead of 3.67 milliliters of propylene glycol. The copolymer was dried under vacuum (0.1 mm Hg) at 110° C. for about 7 hours to remove any unreacted monomer. The copolymer had an inherent viscosity of 0.12 dl/g in hexafluoroisopropanol ( HFIP) at 25° C. The copolymer was a liquid at room temperature. The mole ratio of poly[ε-caprolactone]/poly[lactide]/caprolactone/glycerol ester was found to be 46.5/43.6/2.2/7.7 by NMR.

EXAMPLE 5

LIQUID COPOLYMERS OF ε-CAPROLACTONE/L(−)LACTIDE @ 40/60 BY MOLE PERCENT OF INITIAL COMPOSITION

The procedure in Example 4 was substantially repeated, except that 45.66 gm (0.40 mole) of ε-caprolactone, 86.48 g (0.60 mole) of L(−) lactide were used. The copolymer was dried under vacuum (0.1 mm Hg) at 110° C. for about 7 hours to remove any unreacted monomer. The copolymer had an inherent viscosity of 0.11 dl/g in hexafluoroisopropanol (HFIP) at 25° C. The copolymer was a liquid at room temperature. The mole ratio of poly[ε-caprolactone]poly[lactide]/caprolactone/glycerol ester was found to be 40.4/49.0/1.7/8.9 by NMR.

EXAMPLE 6

LIQUID COPOLYMERS OF ε-CAPROLACTONE/L(−)LACTIDE @35/65 BY MOLE PERCENT INITIAL COMPOSITION

The procedure in Example 4 was substantially repeated, except that 39.95 gm (0.35 mole) of ε-caprolactone, 93.68 g (0.65 mole) of L(−) lactide were used. The copolymer was dried under vacuum (0.1 mm Hg) at 110° C. for about 7 hours to remove any unreacted monomer. The copolymer had an inherent viscosity of 0.12 dl/g in hexafluoroisopropanol (HFIP) at 25° C. The copolymer was a liquid at room temperature. The mole ratio of poly[ε-caprolactone]/poly[lactide]/caprolactone/glycerol ester was found to be 36.3/54.5/1.3/7.9 by NMR.

I claim:

1. A liquid copolymer comprising from in the range of 55 to 70 mole percent lactide and from in the range of 45 to 30 mole percent ε-caprolactone, having an intrinsic viscosity in the range of from about 0.05 to about 0.8 dl/g as determined in a 0.1 g/dl solution of hexafluoroisopropanol at 25° C.

2. The copolymer of claim 1 wherein the amount of lactide in the copolymer is in the range of from 55 to 65 mole percent and the amount of ε-caprolactone is in the range of from 45 to 35 mole percent.

3. The copolymer of claim 2 wherein the copolymers a liquid at 25° C.

4. The copolymer of claim 3 wherein the intrinsic viscosity of the copolymer is between about 0.05 dl/g and about 0.2 dl/g.

5. A copolymer of claim 1 wherein the copolymer is a random copolymer.

* * * * *